United States Patent
Greaney et al.

(10) Patent No.: US 8,877,058 B2
(45) Date of Patent: Nov. 4, 2014

(54) PROCESS FOR SEPARATING SOLUTE MATERIAL FROM AN ALGAL CELL FEED STREAM

(75) Inventors: Mark A. Greaney, Upper Black Eddy, PA (US); James R. Bielenberg, Houston, TX (US); Paul D. Oldenburg, Easton, PA (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 306 days.

(21) Appl. No.: 13/285,834

(22) Filed: Oct. 31, 2011

(65) Prior Publication Data

US 2012/0065415 A1   Mar. 15, 2012

Related U.S. Application Data

(60) Provisional application No. 61/426,577, filed on Dec. 23, 2010.

(51) Int. Cl.
*B01D 11/00* (2006.01)
*C07C 51/48* (2006.01)
*C11B 1/10* (2006.01)

(52) U.S. Cl.
CPC .. *C07C 51/48* (2013.01); *C11B 1/10* (2013.01)
USPC ............ 210/634; 210/639; 210/805; 44/307; 44/605; 47/1.4; 554/21

(58) Field of Classification Search
CPC .... B01D 11/00; B01D 11/02; B01D 11/0288; B01D 11/04; B01D 11/0446; B01D 11/0492; B01D 17/00; C11B 1/10; C11B 1/02; C11B 1/08; C11B 3/006; C11B 3/001; C11B 3/12; C11B 3/16; C10L 11/00; C10L 2200/0469; C10L 2200/0476; C10L 2200/0484; Y02E 50/10; Y02E 50/12; C07C 51/48; C07C 53/126; C07C 57/03
USPC ......... 210/633, 634, 639, 774, 805, 806, 787; 44/301, 307, 605; 435/133–135, 262, 435/267, 271, 272; 47/1.4; 554/12, 14, 20, 554/21, 75; 562/606; 203/39, 47; 422/258, 422/259
See application file for complete search history.

(56) References Cited

U.S. PATENT DOCUMENTS 3,670,888 A * 6/1972 Boroughs et al. ............ 210/774
4,341,713 A * 7/1982 Stolp et al. .................... 554/17
4,542,036 A * 9/1985 Maes et al. .................. 426/601

(Continued)

OTHER PUBLICATIONS

Michael Cooney et al, "Extraction of Bio-oils from Microalgae", Separation & Purification Reviews, vol. 38, pp. 291-321, 2009.*

(Continued)

*Primary Examiner* — Joseph Drodge
(74) *Attorney, Agent, or Firm* — David M. Weisberg

(57) ABSTRACT

This invention provides a process for separating solute material from an algal cell feed stream. The algal cell feed stream, which contains the solute material, can be introduced into on portion of a mixer-settler vessel, and a solvent feed stream can be introduced into another portion of the vessel to mix with the algal cell feed stream, with a goal of separating at least a portion of the solute material from the algal feed stream.

17 Claims, 1 Drawing Sheet

(56) References Cited

U.S. PATENT DOCUMENTS

| | | | |
|---|---|---|---|
| 7,868,195 B2* | 1/2011 | Fleischer et al. | 554/20 |
| 7,883,882 B2* | 2/2011 | Franklin et al. | 435/196 |
| 8,142,659 B2* | 3/2012 | Kale | 210/634 |
| 2008/0188676 A1* | 8/2008 | Anderson et al. | 554/21 |
| 2009/0298159 A1* | 12/2009 | Wu et al. | 435/257.3 |
| 2010/0233761 A1* | 9/2010 | Czartoski et al. | 435/71.1 |
| 2010/0236137 A1* | 9/2010 | Wu et al. | 44/385 |
| 2011/0086386 A1* | 4/2011 | Czartoski et al. | 435/67 |
| 2011/0174734 A1* | 7/2011 | Seibert et al. | 210/650 |
| 2011/0283602 A1* | 11/2011 | Gallop et al. | 44/307 |
| 2011/0287477 A1* | 11/2011 | Tang | 435/68.1 |
| 2012/0021457 A1* | 1/2012 | Tang | 435/68.1 |
| 2012/0022278 A1* | 1/2012 | Aravanis et al. | 554/8 |
| 2012/0040443 A1* | 2/2012 | Wase et al. | 435/271 |
| 2012/0053357 A1* | 3/2012 | Kale | 554/21 |
| 2012/0156717 A1* | 6/2012 | Allnutt et al. | 435/52 |

OTHER PUBLICATIONS

Vermeij et al., "Survival and dispersal of turf algae and macroalgae consumed by herbivorous coral reef fishes", Oecologia, Sep. 4, 2012, p. 417-425, v. 171, Springer-Verlag.

* cited by examiner

PROCESS FOR SEPARATING SOLUTE MATERIAL FROM AN ALGAL CELL FEED STREAM

CROSS-REFERENCE TO RELATED APPLICATIONS

This application relates to and claims priority to U.S. Provisional Patent Application No. 61/426,577 of the same title filed Dec. 23, 2010.

This application is also related to the following co-pending, commonly assigned, applications: (1) U.S. patent application Ser. No. 13/324,607 entitled "Genetically Engineered Microorganisms Comprising 4-Hydroxybenzoyl-CoA Thioesterases and Methods of Using the Same for Producing Free Fatty Acids and Fatty Acid Derivatives" filed Dec. 13, 2011 which claims priority to U.S. Provisional Patent Application No. 61/426,568 of the same title filed Dec. 23, 2010; (2) U.S. patent application Ser. No. 13/324,623 entitled "Prokaryotic Acyl-ACP Thioesterases for Producing Fatty Acids in Genetically Engineered Microorganisms" filed Dec. 13, 2011 which claims priority to U.S. Provisional Patent Application No. 61/426,555 of the same title filed Dec. 23, 2010; (3) U.S. patent application Ser. No. 13/324,636 entitled "Culturing a Microorganism in a Medium with an Elevated Level of a Carboxylate Counterion Source" filed Dec. 13, 2011 which claims priority to U.S. Provisional Patent Application No. 61/426,602 of the same title filed Dec. 23, 2010; and (4) U.S. patent application Ser. No. 13/324,653 entitled "Lipase-Mediated Production of Free Fatty Acids by Recombinant Microorganisms" filed Dec. 13, 2011 which claims priority to U.S. Provisional Patent Application No. 61/426,624 of the same title filed Dec. 23, 2010.

The contents of each of the above applications are hereby incorporated by reference in their entirety.

FIELD OF THE INVENTION

This invention is directed to a process for separating solute material from an algal cell feed stream. More specifically, this invention is directed to separating or extracting solute material from an algal cell feed stream using a solvent, in which the separation or extraction is carried out without substantially rupturing the algal cells and/or without significantly destroying algal cell viability.

BACKGROUND OF THE INVENTION

Separation of solute materials such as hydrocarbon oils produced from algae is somewhat difficult due to the relatively low concentrations of algal cells and solute materials that are generally present in a growth medium. Due to the amount of water present in the growth medium, a relatively large quantity of energy has to be applied to recover the solute material in sufficient quantity.

U.S. Patent Application Publication No. 2009/0163731 discloses a method in which a solute material derived from algae, i.e., triglycerides, can be treated to produce glycerin and biodiesel co-products and those products subsequently separated. The method includes the use of a Podbielniak extractor to separate the co-products, operating in a countercurrent flow regime.

International Publication No. WO 2010/096002 discloses isolating oil from an algae slurry containing the oil. The slurry is feed into a three phase centrifugal separator having a stack of separating discs in which the separator is operated under a force of at least 4500 G. An oil phase, a liquid phase, and a bio-organic phase are obtained as three separate phases. The process includes rupturing the cell walls of the algae to obtain the oil. The oil can be extracted by a solvent such as methanol, ethanol, or ethyl acetate.

Although improvements have been made in recovering desirable solute materials produced from algae, there nevertheless is plenty of room for even more improvement made to make it practical to isolate and recover such materials from algae. There can be significant need for enhanced efficiency of solute recovery. It may also be desirable to separate or extract solute material derived from algae, without having to rupture the cell walls of the algae and/or without significantly destroying algal cell viability.

SUMMARY OF THE INVENTION

This invention produces a relatively high quantity of solute material derived from algae, with a high degree of efficiency. The invention provides the further advantage of separating or extracting the solute material with little if any cellular damage or disruption to the algae cells.

According to an aspect of the invention, a process is provided for separating solute material from algal cells in a feed stream without substantially rupturing the algal cells and/or without significantly destroying algae cell viability. The process comprises: introducing an algal cell feed stream containing solute material external to the algal cells (e.g., which can include at least one $C_4$ to $C_{28}$ fatty acid, optionally which the algal cells themselves produced, and preferably even released) in the feed stream into a vessel; introducing a solvent feed stream (e.g., comprising a plant- and/or algal-derived hydrocarbonaceous liquid, optionally with a similar composition to the solute material) into the vessel to mix with the algal cell feed stream, optionally in a countercurrent direction with respect to each other; separating at least a portion of the solute material from the algal feed stream with the help of the solvent (e.g., a recycled slipstream of which separated solvent plus solute material may at least partially constitute the introduced solvent); removing from the vessel at least a portion the separated solute material and solvent, wherein the solvent introduction, solute separation, and solute removal steps are performed under effective conditions (e.g., including one or more of: a separation force of not greater than about 16000 G; a pH from 7 to 9; a temperature within about 5° C. from the range of the cell's natural habitat and/or from about 10° C. to about 40° C.; and a salinity of at least 2 PSU below that of the salinity level of the cell's natural habitat and/or from about 0 PSU to about 35 PSU) without substantially rupturing the algal cells and/or without significantly destroying algal cell viability; and sending at least the algae cells whose viability has not significantly been destroyed to a separate vessel for combination with other viable algae cells.

Other aspects of the invention are described and/or can be readily apparent to the skilled reader from the disclosure herein.

BRIEF DESCRIPTION OF THE DRAWINGS

Examples of various embodiments of this invention are shown in the attached Figures, wherein.

DETAILED DESCRIPTION OF THE EMBODIMENTS

Introduction

Figure 1:
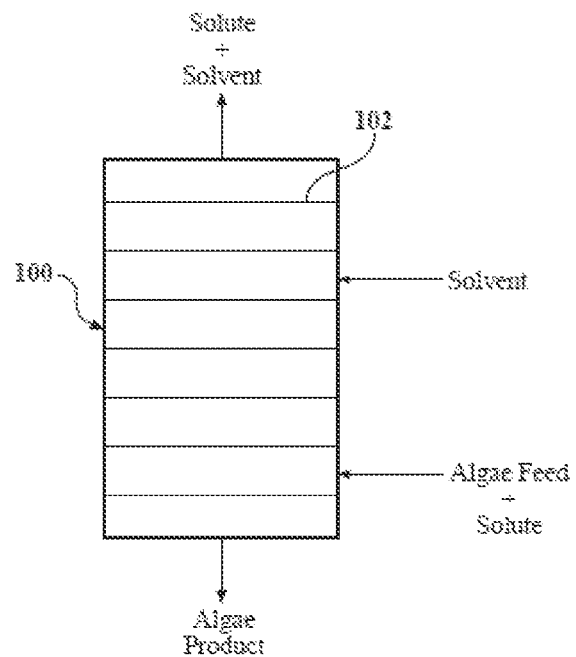
FIG. 1 shows a process flow diagram of an algal cell feed stream being introduced into one end of a mixer-settler vessel, with a solvent stream being introduced into another end of the mixer-settler vessel.

This invention provides a process for separating solute material from an algal cell feed stream. The process can be carried out so as to preserve the integrity and/or viability of a substantial portion of the algal cells, while effectively separating the desirable solute material that is also in the feed stream. In other words, the solute material can be recovered from a feed stream that comprises algae and the solute material, without substantially rupturing the algal cells and/or without significantly destroying algal cell viability.

As used herein, the phrase "without substantially rupturing the algal cells" should be understood to refer to a process that leaves most of the algal cells intact (their cell walls unruptured), e.g., at most 10% of the algal cells can be ruptured, preferably no more than 5% can be ruptured, for example no more than 3% can be ruptured, no more than 2% can be ruptured, no more than 1% can be ruptured, no more than 0.5% can be ruptured, no more than 0.1% can be ruptured, or no observable cells can be ruptured, upon completion of the process steps. Cell rupture can be seen by any method known to one of ordinary skill in the art, e.g., some form of microscopy, plate assay, and/or flow cytometry (optionally with enhanced contrast such as through staining/dying, fluorescence, and/or some other method), and the percentage of cell rupture can be quantified using known/standard statistical methods based on an appropriate counting procedure.

Also as used herein, the phrase "without significantly destroying algal cell viability" should be understood to refer to a process that, for the most part, allows the algal cells to retain their viability or their capability to grow and/or reproduce, e.g., which corresponds to a cell viability of at least 80% (i.e., at least 80% of the cells can be identified as viable through an appropriate viability testing method), preferably a cell viability of at least 85%, such as at least 90%, at least 95%, at least 97%, at least 98%, at least 99%, at least 99.5%, at least 99.9%, or as much as about 100%. Examples of appropriate viability testing methods can be readily determined by one of ordinary skill in the art; for example, cells can be tested for viability using cellular stains that probe the integrity of the cell membrane or colorimetric assays that rely on the metabolic state of the cell. The proportion of viable to non-viable cells can be determined by microscopy, plate assay, flow cytometry, or the like, or some combination thereof. In some embodiments, assays can use fluorogenic esterase substrates (e.g., calcein AM, BCECF AM, various fluorescein diacetate derivatives, and/or the like), nucleic acid stains (e.g., SYTO stains, SYTOX stains, aminoactidimycin D, ethidium/propidium dyes, and/or the like), assays that measure oxidation or reduction (e.g., using indicators such as resazurin, dodecylresazurin, dihydrorhodamines or dihydrofluoresceins, 3,4,5,6-pentafluorotetramethyldihydrorosamine, tetrazolium salts, 3-(4,5-dimethylthiazol-2-yl)-2,5-phenyltetrazolium bromide (MTT), and/or the like). Advantageously, a dye/stain/detection reagent can be selected such that the absorption and/or emission spectra do not significantly overlap that of the pigments of the cells (e.g., chlorophylls and/or phycobilins). Reagents and kits for measuring cell viability are commercially available, for example, from Life Technologies Inc. (Carlsbad, Calif.) and Invitrogen (Carlsbad, Calif.). See also J. M. Capasso et al., *Biomolecular Engineering*, 20 (2003), pp. 133-138; F. Ribalet et al., *Aquatic Toxicology*, 85 (2007), pp. 219-227; and the following website:

http://www.invitrogen.com/site/us/en/home/References/Molecular-Probes-The-Handbook/Assays-for-Cell-Viability-Proliferation-and-Function/Viability-and-Cytotoxicity-Assay-Reagents.html.

Algal Cells and Algal Cell Feed Stream

The algal cell feed stream of this invention can include any unicellular or multicellular algae capable of producing fatty acid. A fatty acid is a carboxylic acid with a long typically unbranched hydrocarbon tail (chain), which can be saturated or unsaturated. The algae used according to this invention can advantageously produce at least one $C_4$ to $C_{28}$ fatty acid.

A "fatty acid", as used herein, is meant to include certain carboxylic acid derivatives and to generally refer to a non-esterified acyl moiety that is substantially not covalently bound, e.g., to an enzyme and/or protein, within or outside an organism (e.g., globular and/or micellular storage within an organism, without esterification, can still qualify as a fatty acid). A carboxylic acid, when produced by a cellular organism, can alternately be termed a "free fatty acid", which includes both acidic and non-acidic forms by convention. Thus, a carboxylic acid, carboxylic acid derivative, or free fatty acid, according to the present invention need not necessarily be a strict acid or be structurally "free", but a carboxylic acid derivative herein specifically does not include an acyl moiety whose carboxylate oxygen is covalently linked to any other moiety besides a hydrogen atom (meaning that fatty acid esters are specifically not included as carboxylic acid derivatives, and thus are specifically not included under the general heading of carboxylic acids herein). However, a free fatty acid (carboxylic acid and/or carboxylic acid derivative) can advantageously include an acyl moiety containing at least four carbons (preferably at least 6 carbons, for example at least 8 carbons, at least 10 carbons, or at least 12 carbons) and typically not greater than 28 carbons (for example not greater than 26 carbons, not greater than 24 carbons, or not greater than 22 carbons), in which the acyl moiety (i) is covalently linked to a hydrogen atom, (ii) has an ionic charge, to which a counterion can be associated (even if loosely and/or solvent-separated), and/or (iii) is otherwise associated (not covalently) with another moiety that is relatively easily transformable into the corresponding acid form or the corresponding ionic form (e.g., through hydrogen-bonding or the like). Nonlimiting examples of counterions can include metals salts (such as calcium, sodium, potassium, aluminum, iron, and the like, and combinations thereof), other inorganic ions (such as ammonium, mono-, di-, tri-, and tetra-alkylammonium, sulfonium, phosphonium, and the like, and combinations thereof), organic ions (such as carbocations), and the like, and combinations thereof.

The algae used according to this invention can optionally but preferably be capable of releasing the solute material through its cell wall(s), such that the solute material to be separated from the feed stream can be (mostly or completely) external to the algal cells in the feed stream. Such an embodiment could enable some (e.g., significant) portion of the algal cells in the algal cell feed stream to be separated and recycled for continued production of solute material.

The algae can be either prokaryotic or eukaryotic. In one embodiment, the algal cells are eukaryotic.

Microalgae are especially useful in this invention. A microalga is generally a single-cell alga having a cell size from about 1 μm to about 100 μm.

Microalgae that are capable of producing $C_4$ to $C_{28}$ fatty acids are especially useful. Examples of classes of such microalgae include, but are not limited to, Bacillariophyceae, Chlorophyceae, Cryptophyceae, Eustigmatophyceae, Prasinophyceae, and Prymnesiophyceae. Examples of genera of the class Bacillariophyceae include, but are not limited to, *Chaetoceros, Nitzchia, Phaeodactylum, Skeletonema*, and *Thalassiosira*. Examples of genera of the class Chlorophyceae include, but are not limited to, *Dunaliella* and *Nannochloris*. An example of a genus of the class Cryptophyceae includes, but is not limited to *Chroomonas*. An example of a genus of the class Eustigmatophyceae includes, but is not limited to, *Nannochloropsis*. An example of a genus of the class Prasinophyceae includes, but is not limited to, *Tetraselmis*. Examples of genera of the class Prymnesiophyceae include, but are not limited to *Isochrysis* and *Pavlova*. Any one or more species of the genus *Nannochloropsis* can be used according to this invention. Examples of such species include, but are not limited to, *N. gaditana, N. granulate, N. limnetica, N. oceanica, N. oculata*, and *N. salina*.

Additionally or alternately, non-limiting examples of microalgae can include, for example, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella*, and *Volvox* species, including freshwater and marine microalgal species of these or other genera.

Further additionally or alternately, the algae used according to the invention can be characterized as cyanobacteria. Non-limiting examples of cyanobacteria can include, for example, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species, including freshwater and marine cyanobacterial species of these or other genera.

Solute Material

The solute material to be separated from the algal cell feed stream according to this invention can be a hydrocarbonaceous material that can be produced by, and optionally but preferably also released from, the algal cells. The term "release," as used herein, with reference to a composition vis-à-vis a cell, shall be understood to encompass both passive and active transport (via secretion/excretion) of the composition across/through a cell membrane (or cell wall, as applicable, and interchangeably used herein), typically from internal to the cell membrane to external to the cell membrane. Though the solute material is described herein as hydrocarbonaceous, it may (and often does) include molecules containing atoms other than carbon and hydrogen, e.g., heteroatoms such as oxygen, nitrogen, phosphorus, sulfur, and the like, and combinations thereof, particularly including, but not limited to, natural cellular products, such as mono-, di-, and tri-glycerides, enzymes, lipids, amino acids, proteins, genetic materials, constituents of cell membranes/walls, organic materials such as carboxylic acids (including the above-defined derivatives), free fatty acids, fatty alcohols, fatty acid esters such as wax esters, ketones, aldehydes, alcohols, and the like, and combinations thereof.

The hydrocarbonaceous solute material that is separated can advantageously include a significant portion of fatty acids, e.g., at least 5 wt % fatty acid, such as at least 10 wt % fatty acid, at least 20 wt % fatty acid, at least 30 wt % fatty acid, or at least 40 wt % fatty acid, based on total weight of the solute in the algal cell feed stream.

The fatty acid component of the solute material in the algal cell feed stream can include at least at least one $C_4$ to $C_{28}$ fatty acid, for example at least one $C_8$ to $C_{24}$ fatty acid and/or at least one $C_{10}$ to $C_{22}$ fatty acid. The fatty acids can be saturated or unsaturated.

Generally, at least about 50 wt % of the total fatty acid component of the solute material in the algal cell feed stream can comprise a mixture of fatty acids having from 8 to 24 carbon atoms. Additionally or alternately, at least about 40 wt % of the total fatty acid component of the solute material in the algal cell feed stream can comprise a mixture of fatty acids having from 8 to 24 carbon atoms. Further additionally or alternately, at least about 30 wt % of the total fatty acid component of the solute material in the algal cell feed stream can comprise a mixture of fatty acids having from 10 to 22 carbon atoms. The fatty acid component can include any one or a combination of the exemplary fatty acid compounds listed hereinbelow.

One example of a fatty acid material that can be separated from the algal cell feed stream is caprylic acid (C8:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be caprylic acid, based on total weight of fatty acid present in the algal cell feed stream, e.g., external to the algal cells.

Another example of carboxylic acid material that can be separated from the algal cell feed stream is capric acid (C10:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be capric acid, based on total weight of fatty acid present in the algal cell feed stream, e.g., external to the algal cells.

Another example of carboxylic acid material that can be separated from the algal cell feed stream is lauric acid (C12:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be lauric acid, based on total weight of fatty acid present in the algal cell feed stream, e.g., external to the algal cells.

Another example of carboxylic acid material that can be separated from the algal cell feed stream is myristic acid (C14:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be myristic acid, based on total weight of fatty acid present in the algal cell feed stream, e.g., external to the algal cells.

Another example of carboxylic acid material that can be separated from the algal cell feed stream is palmitic acid (C16:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be palmitic acid, based on total weight of fatty acid present in the algal cell feed stream, e.g., external to the algal cells.

Another example of carboxylic acid material that can be separated from the algal cell feed stream is palmitoleic acid (C16:1). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be palmitoleic acid, based on total weight of fatty acid present in the algal cell feed stream, e.g., external to the algal cells.

Another example of carboxylic acid material that can be separated from the algal cell feed stream is sapienic acid (C16:2). In an embodiment, when present, from about 0.1 wt % to about 60 wt %, for example from about 0.1 wt % to about 45 wt % or from about 0.1 wt % to about 30 wt %, of the fatty acid material in the algal cell feed stream external to the algal cells can be sapienic acid, based on total weight of fatty acid present in the algal cell feed stream, e.g., external to the algal cells.

Another example of carboxylic acid material that can be separated from the algal cell feed stream is stearic acid (C18: 0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be stearic acid, based on total weight of fatty acid present in the algal cell feed stream, e.g., external to the algal cells.

Another example of carboxylic acid material that can be separated from the algal cell feed stream is oleic acid (C18:1). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be oleic acid, based on total weight of fatty acid present in the algal cell feed stream, e.g., external to the algal cells.

Another example of carboxylic acid material that can be separated from the algal cell feed stream is linoleic acid (C18:2). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be linoleic acid, based on total weight of fatty acid present in the algal cell feed stream, e.g., external to the algal cells.

Another example of carboxylic acid material that can be separated from the algal cell feed stream is linolenic acid (C18:3). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be linolenic acid, based on total weight of fatty acid present in the algal cell feed stream, e.g., external to the algal cells.

Another example of carboxylic acid material that can be separated from the algal cell feed stream is arachidic acid (C20:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be arachidic acid, based on total weight of fatty acid present in the algal cell feed stream, e.g., external to the algal cells.

Another example of carboxylic acid material that can be separated from the algal cell feed stream is eicosenoic acid (C20:1). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be eicosenoic acid, based on total weight of fatty acid present in the algal cell feed stream, e.g., external to the algal cells.

Another example of carboxylic acid material that can be separated from the algal cell feed stream is eicosadienoic acid (C20:2). In an embodiment, when present, from about 0.1 wt % to about 60 wt %, for example from about 0.1 wt % to about 45 wt % or from about 0.1 wt % to about 30 wt %, of the fatty acid material in the algal cell feed stream external to the algal cells can be eicosadienoic acid, based on total weight of fatty acid present in the algal cell feed stream, e.g., external to the algal cells.

Another example of carboxylic acid material that can be separated from the algal cell feed stream is mead acid (C20: 3). In an embodiment, when present, from about 0.1 wt % to about 60 wt %, for example from about 0.1 wt % to about 45 wt % or from about 0.1 wt % to about 30 wt %, of the fatty acid material in the algal cell feed stream external to the algal cells can be mead acid, based on total weight of fatty acid present in the algal cell feed stream, e.g., external to the algal cells.

Another example of carboxylic acid material that can be separated from the algal cell feed stream is arachidonic acid (C20:4). In an embodiment, when present, from about 0.1 wt % to about 60 wt %, for example from about 0.1 wt % to about 45 wt % or from about 0.1 wt % to about 30 wt %, of the fatty acid material in the algal cell feed stream external to the algal cells can be arachidonic acid, based on total weight of fatty acid present in the algal cell feed stream, e.g., external to the algal cells.

Another example of carboxylic acid material that can be separated from the algal cell feed stream is eicosapentanoic acid (C20:5). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be eicosapentanoic acid, based on total weight of fatty acid present in the algal cell feed stream, e.g., external to the algal cells.

Another example of carboxylic acid material that can be separated from the algal cell feed stream is behenic acid (C22:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be behenic acid, based on total weight of fatty acid present in the algal cell feed stream, e.g., external to the algal cells.

Another example of carboxylic acid material that can be separated from the algal cell feed stream is erucic acid (C22: 1). In an embodiment, when present, from about 0.1 wt % to about 60 wt %, for example from about 0.1 wt % to about 45 wt % or from about 0.1 wt % to about 30 wt %, of the fatty acid material in the algal cell feed stream external to the algal cells can be erucic acid, based on total weight of fatty acid present in the algal cell feed stream, e.g., external to the algal cells.

Another example of carboxylic acid material that can be separated from the algal cell feed stream is lignoceric acid (C24:0). In an embodiment, when present, from about 0.5 wt % to about 95 wt %, for example from about 0.5 wt % to about 75 wt % or from about 0.5 wt % to about 50 wt %, of the fatty acid material in the algal cell feed stream external to the algal cells can be lignoceric acid, based on total weight of fatty acid present in the algal cell feed stream, e.g., external to the algal cells.

Another example of carboxylic acid material that can be separated from the algal cell feed stream is nervonic acid (C24:1). In an embodiment, when present, from about 0.1 wt % to about 60 wt %, for example from about 0.1 wt % to about 45 wt % or from about 0.1 wt % to about 30 wt %, of the fatty acid material in the algal cell feed stream external to the algal cells can be nervonic acid, based on total weight of fatty acid present in the algal cell feed stream, e.g., external to the algal cells.

The solute material that is comprised in the algal cell feed stream can be at a high enough concentration so that it can be effectively recovered from the feed stream. In an embodiment, the solute material can be at a concentration of at least about 2000 wppm, based on total weight of the feed stream. In some embodiments, more concentrated streams can be preferred. For example, algal cell feed streams can contain concentrations of solute material of at least about 5000 wppm, such as at least about 10000 wppm, at least about 50000 wppm, at least about 100000 wppm, or at least about 200000 wppm, based on total weight of the feed stream.

The amount of algal cells in the feed stream can advantageously be sufficiently high for purposes of producing and/or releasing an appropriate concentration of the solute material, but not so high as to negatively impact (e.g., significantly destroy) cell viability and/or to prevent flow into the separation vessel. For example, the weight of the algal cells (based on dry weight) in the feed stream can be at least about five times, for example at least about ten times, at least about fifteen times, at least about twenty times, at least about twenty-five times, at least about thirty times, at least about thirty-five times, at least about forty times, at least about forty-five times, or at least about fifty times that of the solute material in the feed stream.

In some embodiments, to maintain high cell integrity and viability of the algal cells in an aqueous feed stream containing fatty acids as solute material, the feed stream can contain an increased concentration of a metal (typically provided as a salt and/or in an ionic form) such as, for example, sodium, potassium, magnesium, calcium, iron, strontium, chromium, manganese, cobalt, nickel, copper, zinc, aluminum, or the like, or combinations thereof (particularly multivalent metals, such as magnesium, calcium, and/or iron), with respect to a standard cell medium growth formulation, such as, for example, standard BG-11 medium (ATCC Medium 616, Table 2), or a modified medium such as ATCC Medium 854 (BG-11 modified to contain vitamin B12) or ATCC Medium 617 (BG-11 modified for marine cyanobacteria, containing additional NaCl and vitamin B12).

For example, the algal cell feed stream can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g., calcium) as compared to a standard cell growth medium. Additionally or alternatively, the algal cell feed stream can include, for example, at least about 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g., calcium) content in the feed stream.

In further embodiments, by using the excess amount of metal (e.g., calcium) in the feed stream, at least a portion of the fatty acid(s) can be sequestered as carboxylate precipitates, which may result in decreasing the toxic effects of the fatty acid(s) from the solute material. Addition of metal (e.g., calcium) in the feed stream can additionally or alternatively increase the tolerance of algal cells in the feed stream with a relatively high concentration of fatty acids. Additionally or alternatively, fatty acid-producing algal strains can advantageously be more robust/viable with excess metal (e.g., calcium) content. Although the excess component is described herein as a metal, it is contemplated that the component can more generally be described as a carboxylate counterion source, for example an inorganic counterion source, a metal counterion source (noted as "metal" herein), a multivalent (i.e., having a valence of +2 or higher) counterion source, a divalent counterion source, or some combination. Other details regarding this metal/carboxylate counterion source are described in the co-pending, commonly-assigned patent application, entitled "Culturing a Microorganism in a Medium with an Elevated Level of a Carboxylate Counterion Source" and filed on the same day herewith.

Solvent

The solvent according to this invention can be a hydrocarbonaceous liquid, e.g., that can be effective in extracting the desired solute material from the algal cell feed stream. The closer the characteristics of the solvent to the solute material are, the greater the efficiency tends to be in removing the solute material from the algal cell feed stream.

Thus, in one embodiment, the solvent can comprise a plant- or algal-derived hydrocarbonaceous liquid, such as a plant extract/oil, an algae oil, a pyrolysis oil, or the like, or a combination thereof Non-limiting examples of plant extracts/oils can include rapeseed oil, canola oil, soybean oil, coconut oil, sunflower oil, palm oil, palm kernel oil, peanut oil, linseed oil, camelina oil, safflower oil, babassu oil, tallow oil, flaxseed oil, tall oil, rice bran oil, a distilled fraction thereof, an oil component thereof, or a combination thereof Non-limiting examples of algae oils can include one or more fractions of the solute material separated from the algal cell feed stream, optionally in combination with another algae oil. One specific example of such an algae oil fraction can be a slipstream portion (i.e., a minor fraction) of the solute material separated in the separator vessel.

Additionally or alternatively, the solvent can comprise a $C_1$ to $C_5$ alkyl ester of a $C_4$ to $C_{28}$ fatty acid, such as a FAME. Further additionally or alternatively, the solvent can comprise at least one $C_4$ to $C_{28}$ fatty acid, preferably at least one $C_8$ to $C_{24}$ fatty acid, e.g., at least one $C_{10}$ to $C_{22}$ fatty acid.

The fatty acid contained in the solvent can, in many embodiments, comprise a mixture of fatty acids. For instance, the mixture of fatty acids can include at least two $C_{12}$ to $C_{24}$ fatty acids, preferably at least two unsaturated $C_{12}$ to $C_{24}$ fatty acids. Non-limiting specific examples of the fatty acids that can be present in the mixture can include those described above with reference to the algal cell feed stream.

In certain embodiments, the solvent can advantageously comprise a composition similar to the solute material, which can include a significant portion of fatty acids, e.g., at least 5 wt % fatty acid, such as at least 10 wt % fatty acid, at least 20 wt % fatty acid, at least 30 wt % fatty acid, or at least 40 wt % fatty acid, based on total weight of the solvent supplied to the separator vessel.

Additionally or alternately in embodiments when the solvent comprises fatty acids, at least about 50 wt % of the fatty acid portion of the solvent supplied to the separator vessel can comprise a mixture of fatty acids having from 8 to 24 carbon atoms. Further additionally or alternately in embodiments when the solvent comprises fatty acids, at least about 40 wt % of the fatty acid portion of the solvent supplied to the separator vessel can comprise a mixture of fatty acids having from 8 to 24 carbon atoms. Still further additionally or alternately in embodiments when the solvent comprises fatty acids, at least about 30 wt % of the fatty acid portion of the solvent supplied to the separator vessel can comprise a mixture of fatty acids having from 10 to 22 carbon atoms.

The solvent can, in various embodiments, have a density less than that of water. For example, the solvent can have a density of 0.99 g/cc or less at about 25° C., for example a density of about 0.95 g/cc or less, about 0.9 g/cc or less, or about 0.85 g/cc or less (all at about 25° C.).

Of course the solvent should be soluble (miscible) with the solute material, but it can be desirable in some embodiments that the solvent not be too soluble in (miscible with) water, e.g., such that the solvent and solute material can be effectively separated from the water in the separator vessel, e.g., from the algal cell feed stream. In one example, the solvent can have a solubility in water of not greater than 10 g/L at about 20° C., for example not greater than 5 g/L, not greater than 1 g/L, or not greater than 0.5 g/L (all at about 20° C.).

The amount of solvent used according to this invention can be based on a ratio of solvent to algal cell feed stream, on an algal cell dry weight basis (excluding intracellular water). Depending on the carboxylic acid content, the solvent can be introduced into the treat or mix vessel at a ratio of solvent to algae from about 1:10 to about 10:1, for example from about 1:10 to about 1:1 or from about 1:1 to about 1:10, based on algal cell dry weight.

Vessel

The vessel in which treatment of the feed stream to separate and remove the solute material can be any vessel suitable for mixing. In one embodiment, mixing of solute and solvent can be carried out in one vessel, while separating the solute from the algal cell feed stream or algal material can be carried out in another vessel. In such an embodiment, mixing can be carried out in a mix vessel, and separating can be carried out in a separator such as a centrifuge.

Alternately, mixing and separating can be carried out in the same vessel. Examples of such vessels include, but are not limited to, mixer-settlers, sieve plate settlers (e.g., perforated tray towers), and centrifugal separators (e.g., Podbielniak separators). Separating vessels can generally include plates or packing that can provide enhanced mixing of components. Preferably, the separator vessel can include at least one separation zone in which at least a portion of the solute material can be separated from the algal cell feed stream and/or solvent. In one embodiment, at least a portion of metal surfaces internal to the separating vessel can be electropolished, e.g., to reduce adhesion of the algal cells to the metal surfaces and/or to reduce corrosion of the metal surfaces. Additionally or alternatively, the separator vessel can include internal sieve plates, at least a portion of which can be electropolished.

In embodiments where mixing and separation can occur in the same vessel, the algal cell feed stream can be introduced into one portion of the vessel, while the solvent feed stream is separately introduced, e.g., into another portion of the vessel. In such embodiments, the different streams can be introduced in countercurrent flow directions.

As the solvent contacts the solute material, the solute material can be extracted or separated from the algal cell feed stream, leaving a significant portion of the algal cells associated with an aqueous phase in a treated stream. This treating can preferably be carried out with minimal disruption of the algal cells, e.g., without substantially rupturing the algal cells and/or without significantly destroying algal cell viability.

The relative flow rates of the algal cell feed stream and the solvent stream can be controlled, e.g., so that extraction of the solute material from the algal cell feed stream can properly take place. In various embodiments, the volumetric rate of flow of the algal cell feed stream to the solvent stream can be maintained at an average ratio from about 100:1 to about 1:10, for example from about 50:1 to about 5:1 or from about 5:1 to about 2:1.

Separation of the extracted or separated solute material from the algal cell feed stream can be enhanced by providing a separating force, such as by a applying a centrifugal force. An appropriately applied separation force can effectively separate the solute material from the algal cells, preferably while leaving the algal cells largely intact and/or viable. Thus, in an embodiment, separation can be carried out by applying a separation force of at least about 500 G, for example at least about 1000 G, at least about 2000 G, at least about 3000 G, or at least about 5000 G. Additionally or alternately, separation can be carried out by applying a separation force of not greater than about 16000 G, for example not greater than about 15000 G, not greater than about 12000 G, or not greater than about 10000 G.

A preferred separation vessel is one in which countercurrent contact of solvent with solute can be carried out and in which a separation force can be applied during the countercurrent contact. An example of this type of separator is a Podbielniak separator.

Operating Conditions in Vessel

The vessel(s) used for treating and removing the desired solute material from the algal cell feed stream can advantageously be operated at conditions to preserve cell integrity and viability. Such conditions can include appropriate pH, temperature, and salinity conditions, inter alia.

In various embodiments, the pH within the vessel can be maintained within the range from 7 to 9, for example from 8.2 to 8.7.

Temperature within the vessel(s) can be a temperature high enough to ensure effective solvent and solute material interaction, but low enough (within a range) to preserve cell integrity and viability. In an embodiment, the temperature can be maintained within about 5° C. from the range of the cell's natural habitat, for example from about 10° C. to about 40° C. or from about 18° C. to about 35° C.

Salinity is a factor of greater concern for marine algal cells. Salinity can be measured as PSU, an abbreviation for practical salinity unit, a standard measure of the salinity of seawater. The "unit" is a dimensionless ratio obtained by measuring the conductivity of the water sample. Seawater of salinity 35 PSU has approximately the same conductivity as a standard solution of potassium chloride (KCl) with a concentration of 3.24356% by mass. For example, a sample having a salinity of 1 PSU would have conductivity of $1/35$ that of the standard solution. With this definition, measurements in PSU are very nearly the same as direct measurements of salt ion concentration in parts per thousand.

In various embodiments, the salinity within the vessel can be maintained within a range from about 0 PSU to about 35 PSU. For marine algal cells, salinity can in some embodiments be maintained at a level of at least 2 PSU, for example at least 3 PSU, below that of the salinity of the cell's natural habitat.

Solute Material Recovery

The extracted or separated solute material can be recovered from the vessel along with at least a portion of the solvent. In some embodiments, at least a portion of the solvent can be further separated from the extracted solute material, and the separated solvent can then optionally be used as a part of the solvent stream introduced into the vessel, e.g., as a solvent recycle stream.

In one exemplary embodiment, a mixture of the extracted solute and solvent can be separated from the algal cells, and a portion of the mixture (e.g., a slipstream) can be separated and recycled for re-use as solvent. Additionally or alternately, a mixture of the extracted solute and solvent can be separated from the algal cells and distilled into fractions, one or more of which can then be recycled for use as solvent.

In embodiments where distillation is used, vacuum distillation can be utilized for separation processes. Non-limiting examples of other separation processes can include use of semi-permeable membranes, reverse osmosis, supercritical separation, regenerable lipophilic adsorbents, and combinations thereof.

Additional Embodiments

Additionally or alternately, the present invention can include one or more of the following embodiments.

Embodiment 1. A process for separating solute material from algal cells in a feed stream without substantially rupturing the algal cells and/or without significantly destroying algae cell viability, the process comprising: introducing an algal cell feed stream containing solute material external to the algal cells in the feed stream into a vessel; introducing a solvent feed stream into the vessel to mix with the algal cell feed stream; separating at least a portion of the solute material from the algal feed stream with the help of the solvent; removing from the vessel at least a portion the separated solute material and solvent, wherein the solvent introduction, solute separation, and solute removal steps are performed under effective conditions without substantially rupturing the algal cells and/or without significantly destroying algal cell viability; and sending at least the algae cells whose viability has not significantly been destroyed to a separate vessel for combination with other viable algae cells.

Embodiment 2. The process of embodiment 1, wherein the algal cells are microalgae capable of producing $C_4$ to $C_{28}$ carboxylic acids and belong to at least one of the following classes: Bacillariophyceae, Chlorophyceae, Cryptophyceae, Eustigmatophyceae, Prasinophyceae or Prymnesiophyceae.

Embodiment 3. The process of embodiment 2, wherein the microalgae include at least one species of the genus *Nannochloropsis*.

Embodiment 4. The process of any one of the preceding embodiments, wherein the solute material is a hydrocarbonaceous material comprising at least one $C_4$ to $C_{28}$ fatty acid.

Embodiment 4. The process of any one of the preceding embodiments, wherein the solvent feed stream and the algal cell feed stream are introduced into the vessel so as to mix in a countercurrent direction, and optionally wherein the solvent feed stream is comprised of a slipstream of the separated solute material and solvent that is removed from the vessel.

Embodiment 5. The process of any one of the preceding embodiments, wherein the solvent feed stream has a density less than that of water and a solubility in water of not greater than 10 g/L at about 20° C.

Embodiment 6. The process of any one of the preceding embodiments, wherein the solvent comprises a plant- or algal-derived hydrocarbonaceous liquid and contains at least one $C_4$ to $C_{28}$ fatty acid and/or at least 10 wt % of one or more fatty acids.

Embodiment 7. The process of any one of the preceding embodiments, wherein the vessel is a mixer-settler, sieve plate settler, or a centrifugal separator.

Embodiment 8. The process of any one of the preceding embodiments, wherein separation is carried out at a separation force of not greater than about 16000 G.

Embodiment 9. The process of any one of the preceding embodiments, wherein mixing and separating are carried out at one or more of the following conditions: a pH from 7 to 9; a temperature within about 5° C. from the range of the cell's natural habitat and/or from about 10° C. to about 40° C.; and a salinity of at least 2 PSU below that of the salinity level of the cell's natural habitat and/or from about 0 PSU to about 35 PSU.

Embodiment 10. The process of any one of the previous embodiments, wherein a portion the separated solute material and solvent is separated and recycled as solvent.

Embodiment 11. The process of any one of the previous embodiments, wherein at least a portion the separated solute material and solvent is separated and distilled into fractions, and at least one fraction is recycled as solvent.

Further additionally or alternately, there can be a process according to any one of the preceding process embodiments, wherein the algal cell feed stream can include an increased concentration of a carboxylate counterion source (e.g., an inorganic counterion source, a metal counterion source, a multivalent counterion source, a divalent counterion source, or some combination thereof, such as sodium, potassium, magnesium, calcium, iron, strontium, chromium, manganese, cobalt, nickel, copper, zinc, aluminum, or combinations thereof, particularly multivalent metals, such as magnesium, calcium, and/or iron), with respect to a standard cell medium growth formulation (e.g., standard BG-11 medium) or a modified medium (e.g., ATCC Medium 854 or ATCC Medium 617), which increased concentration can optionally be at least about 0.5 mM (e.g., between about 0.5 mM and about 1 mM, between about 1 mM and about 2 mM, between about 2 mM and about 5 mM, between about 5 mM and about 10 mM, between about 10 mM and about 25 mM, and/or greater than 25 mM) and/or can optionally but preferably be at least 2-fold (e.g., at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold) as compared to said standard/modified cell growth medium.

EXAMPLES

Figure 2:
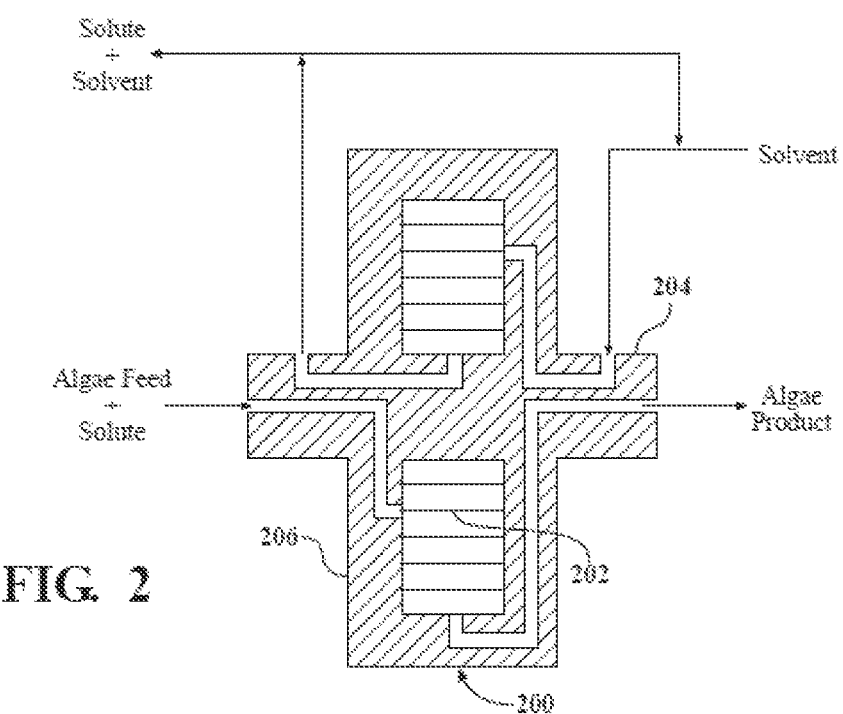
FIG. 2 shows a process flow diagram of an algal cell feed stream being introduced into a conduit that runs through a shaft of a Podbielniak-type extractor, with a solvent stream being introduced into another portion of the shaft of the extractor.

Examples According to FIGS. 1 and 2

According to the embodiment of FIG. 1, an algal cell feed stream is injected into one end of a mixer-settler vessel 100, with a solvent stream being injected into another end of the mixer-settler vessel. The streams are at desired densities that allow the streams to move in countercurrent direction to one another. In FIG. 1, the solvent moves in a downward direction, while the algal cell feed stream moves in an upward direction. As the streams move in their respective directions, they are mixed by way of sieve plates 102, with the solute material in the algal cell feed stream being extracted/separated and recovered at the upper portion of the vessel. The algae product can be recovered at the lower end of the vessel.

The solute material is less dense and can move upward, while the algal stream can move downward.

The embodiment of FIG. 2 uses a Podbielniak-type (POD) extractor 200 as the separator or extractor vessel. In this embodiment, sieve trays 202 are also employed. The extractor is comprised of a shaft 204 and a rotor section 206. The rotor section can be rotated about the shaft to exert a separation force by way of centrifugal rotation about the shaft. The algal cell feed stream is injected by way of a conduit arranged within the shaft to flow the feed stream to the rotor section. The solvent stream is injected by way of a separate conduit also arranged within the shaft to flow the solvent stream into the rotor section, such that the streams flow countercurrently across the sieve trays. The solute material that accompanies the algal cell feed stream can be extracted/separated from the stream and recovered by way of a separate conduit from the shaft. An algae product can also be separated and recovered through a separate conduit from the shaft. If desired, at least a portion of the solvent can be separated from the solute stream that exits the shaft and recycled back to the solvent feed stream. This embodiment uses the POD in what is termed "extraction mode." The POD can also be run in a mode in which the two liquid streams are mixed outside of the POD, and then the mixed stream is fed to the middle of the POD, providing fewer theoretical stages of extraction.

Example Using *Nannochloropsis* sp.

About 6.35 grams of canola oil were added to about 7.2 grams of a medium containing *Nannochloropsis* sp. (about 8 wt % dry solids content). The oil and medium were mixed in a Brinkman Polytron PT3100 mixer for about 15 minutes at room temperature (about 20-25° C.). The mixture was then centrifuged in a Sorvall RC-5B refrigerated centrifuge at about 15,000 rpm for about 30 minutes. Four layers were formed. The least dense (i.e., top) layer appeared as a clear, dilute green liquid. A thin, second layer was formed between the top, clear layer and the third layer, which was the largest layer by volume. This third layer was a dark green heterogeneous layer, similar to the initial medium containing the *Nannochloropsis* sp. The fourth or bottom layer was a thin layer of light-colored solid material. The layers were separated. The top layer was found to contain approximately 3 wt % $C_{16}$ fatty acids (carboxylic acids). This level of $C_{16}$ fatty acids were greater than that observed in the canola oil feed. The fourth or bottom layer was found to contain calcium phosphate.

Prophetic Example Using Cyanobacteria.

In this Example, about 6.35 grams of canola oil is added to about 7.2 grams of a medium containing a genetically engineered *Synechocystis* sp. including a gene (e.g., encoding an acyl-ACP thioesterase) whose expression results in production of free fatty acids (about 8 wt % dry solids content of algae in the medium). The oil and medium are mixed in a Brinkman Polytron PT3100 mixer for about 15 minutes at room temperature (about 20-25° C.). The mixture is then centrifuged in a Sorvall RC-5B refrigerated centrifuge at about 15,000 rpm for about 30 minutes. Four layers can be formed. The least dense (i.e., top) layer can appear as a clear, dilute green liquid. A thin, second layer can be formed between the top, clear layer and the third layer, which is believed to be the largest layer by volume. This third layer can be a dark green heterogeneous layer, similar to the initial medium containing the *Synechocystis* sp. The fourth or bottom layer can be a thin layer of light-colored solid material. The layers can be separated. The top layer can be found to contain an observable amount of free fatty acids (carboxylic acids) greater than that observable in the canola oil feed. The fourth or bottom layer can be found to contain calcium phosphate.

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A process for separating solute material from algal cells in a feed stream without substantially rupturing the algal cells and/or without significantly destroying algae cell viability, the process comprising:
   introducing an algal cell feed stream containing solute material external to the algal cells in the feed stream into a vessel;
   introducing a solvent feed stream into the vessel to mix with the algal cell feed stream;
   separating at least a portion of the solute material from the algal feed stream with the help of the solvent;
   removing from the vessel at least a portion of the separated solute material and solvent, wherein the solvent introduction, solute separation, and solute removal steps are performed under effective conditions without substantially rupturing the algal cells and without significantly destroying algal cell viability, the effective conditions comprising a temperature of about 10° C. to about 40° C. and simultaneously within a range from about 5° C. above to about 5° C. below that of a natural habitat of the algal cells, a separation force of exerted on the algal cells of at least 1,000 G and not greater than 15,000 G, a pH from about 7 to about 9, and a salinity of about 0 PSU to about 35 PSU and simultaneously at least 2 PSU below that of a salinity level of a natural habitat of the algal cells during the mixing and separating; and
   sending at least algal cells whose viability has not significantly been destroyed to a separate vessel for combination with other viable algal cells,
   wherein the solvent comprises one or more hydrocarbonaceous liquids, $C_1$ to $C_5$ alkyl esters of $C_4$ to $C_{28}$ fatty acids, $C_4$ to $C_{28}$ fatty acids, or a combination thereof, and
   wherein performing the solvent introduction, solute separation, and solute removal steps without significantly destroying algal cell viability corresponds to a cell viability of at least 80%.

2. The process of claim 1, wherein the algal cells are micro-algae capable of producing $C_4$ to $C_{28}$ fatty acids.

3. The process of claim 2, wherein the microalgae are algae belonging to at least one class selected from the group consisting of Bacillariophyceae, Chlorophyceae, Cryptophyceae, Eustigmatophyceae, Prasinophyceae and Prymnesiophyceae.

4. The process of claim 3, wherein microalgae are algae belonging to the class Eustigmatophyceae.

5. The process of claim 4, wherein the microalgae include at least one species of the genus *Nannochloropsis*.

6. The process of claim 1, wherein the solute material is a hydrocarbon material comprised of at least one $C_4$ to $C_{28}$ fatty acid.

7. The process of claim 1, wherein the solvent feed stream and the algal cell feed stream are introduced into the vessel so as to mix in a countercurrent direction.

8. The process of claim 1, wherein the solvent feed stream is comprised of a slipstream of the separated solute material and solvent that is removed from the vessel.

9. The process of claim 8, wherein the solvent feed stream has a density less than that of water and a solubility in water of not greater than 10 g/L at about 20° C.

10. The process of claim 8, wherein the solvent comprises at least one $C_4$ to $C_{28}$ fatty acid.

11. The process of claim 10, wherein the solvent introduced into the vessel has a total fatty acid concentration of at least 10 wt %.

12. The process of claim 1, wherein the solvent is a plant or algal derived liquid hydrocarbon.

13. The process of claim 1, wherein the vessel is a mixer-settler, sieve plate settler or a centrifugal separator.

14. The process of claim 1, wherein mixing and separating are carried out at a pH from 8.2 to 8.7.

15. The process of claim 1, wherein a portion the separated solute material and solvent is separated and recycled as solvent.

16. The process of claim 1, wherein at least a portion of the separated solute material and solvent is separated and distilled into fractions, and at least one fraction is recycled as solvent.

17. The process of claim 1, wherein performing the solvent introduction, solute separation, and solute removal steps without significantly destroying algal cell viability corresponds to a cell viability of at least 90%.

* * * * *